(12) United States Patent
Sabbagh et al.

(10) Patent No.: US 7,922,854 B2
(45) Date of Patent: Apr. 12, 2011

(54) LOW COST MULTILAYER ELASTOMERIC FILMS HAVING A LOW PERMANENT SET

(75) Inventors: Amiel B. Sabbagh, Williamsburg, VA (US); Martin F. Hoenigmann, Chippewa Falls, WI (US)

(73) Assignee: Pliant, LLC, Evansville, IN (US)

( * ) Notice: Subject to any disclaimer, the term of this patent is extended or adjusted under 35 U.S.C. 154(b) by 0 days.

(21) Appl. No.: 12/633,613

(22) Filed: Dec. 8, 2009

(65) Prior Publication Data

US 2010/0081353 A1 Apr. 1, 2010

Related U.S. Application Data

(62) Division of application No. 11/432,083, filed on May 11, 2006, now Pat. No. 7,629,278.

(60) Provisional application No. 60/692,308, filed on Jun. 20, 2005.

(51) Int. Cl.
*B29C 47/00* (2006.01)
*B32B 37/00* (2006.01)
*C08J 5/00* (2006.01)

(52) U.S. Cl. .......... 156/244.11; 156/260; 156/308.2; 264/46.1; 264/45.1; 264/45.8; 264/45.9; 422/394; 422/398

(58) Field of Classification Search .......... 156/260, 156/308.2, 244.11; 442/394, 398
See application file for complete search history.

(56) References Cited

U.S. PATENT DOCUMENTS

| | | | |
|---|---|---|---|
| 4,677,017 A | 6/1987 | DeAntonis et al. | |
| 5,139,878 A | 8/1992 | Kim et al. | |
| 5,807,368 A * | 9/1998 | Helmer | 604/373 |
| 6,855,223 B2 | 2/2005 | Johnson | |
| 6,949,283 B2 | 9/2005 | Kollaja et al. | |
| 7,629,278 B2 | 12/2009 | Sabbagh et al. | |
| 2003/0017345 A1 | 1/2003 | Middlesworth et al. | |
| 2003/0134126 A1 | 7/2003 | Hamulski et al. | |
| 2003/0181584 A1 | 9/2003 | Handlin | |
| 2004/0049836 A1 | 3/2004 | Ashraf et al. | |
| 2004/0087235 A1 | 5/2004 | Morman et al. | |
| 2004/0122408 A1 | 6/2004 | Potnis et al. | |
| 2004/0122409 A1 | 6/2004 | Thomas et al. | |
| 2005/0043460 A1 | 2/2005 | McCormack et al. | |
| 2005/0101206 A1 | 5/2005 | McCormack et al. | |
| 2005/0107550 A1 | 5/2005 | Agrawal | |
| 2005/0148730 A1 | 7/2005 | Day et al. | |
| 2005/0197464 A1 | 9/2005 | Handlin et al. | |
| 2005/0215717 A1 | 9/2005 | Dozeman | |
| 2005/0282028 A1 | 12/2005 | Huber | |
| 2005/0288393 A1 | 12/2005 | Lean et al. | |

FOREIGN PATENT DOCUMENTS

| EP | 0885260 | 12/1998 |
|---|---|---|
| WO | 97/32928 | 9/1997 |
| WO | 2005/065932 | 7/2005 |

OTHER PUBLICATIONS

International Search Report in PCT/US06/16312, dated Aug. 17, 2006.
Office Action in U.S. Appl. No. 11/432,083, dated Jul. 24, 2008.
Office Action in U.S. Appl. No. 11/432,083, dated Jun. 1, 2009.
Office Action in U.S. Appl. No. 11/432,083, dated Mar. 19, 2008.
Office Action in U.S. Appl. No. 11/432,083, dated Oct. 7, 2008.

* cited by examiner

*Primary Examiner* — Lynda Salvatore
(74) *Attorney, Agent, or Firm* — Barnes & Thornburg LLP

(57) ABSTRACT

The presently described technology provides a low cost multilayer elastomeric film containing at least one layer of styrene block copolymer and at least one elastomer layer substantially free of styrene block copolymer such that the resultant film has a low permanent set substantially equal to or less than a film comprised of styrene block copolymer only. The elastomeric film may be used in elasticized features of various articles, such as disposable absorbent articles. Methods for producing the low cost elastomeric film having a low permanent set are also described.

20 Claims, 11 Drawing Sheets

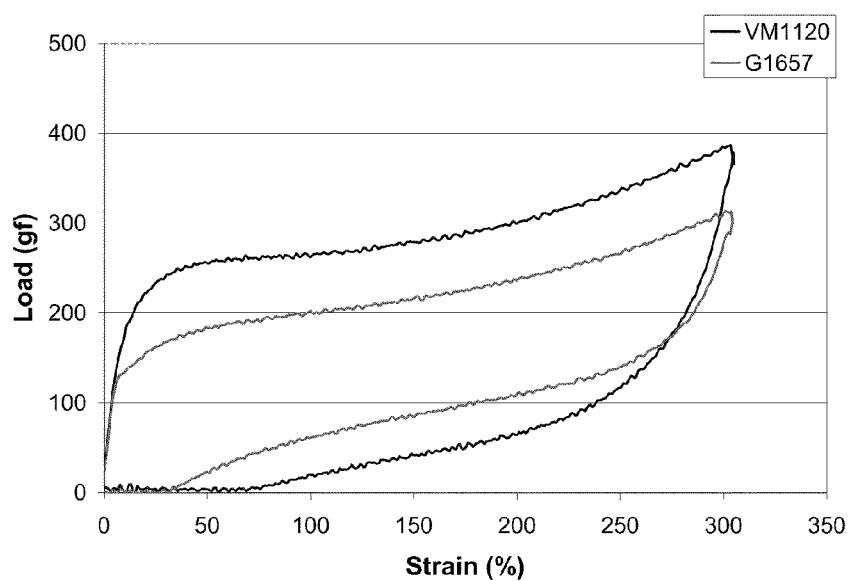
Figure 1. First hysteresis curve, "activation curve" for Kraton G1657 and Vistamaxx VM1120.

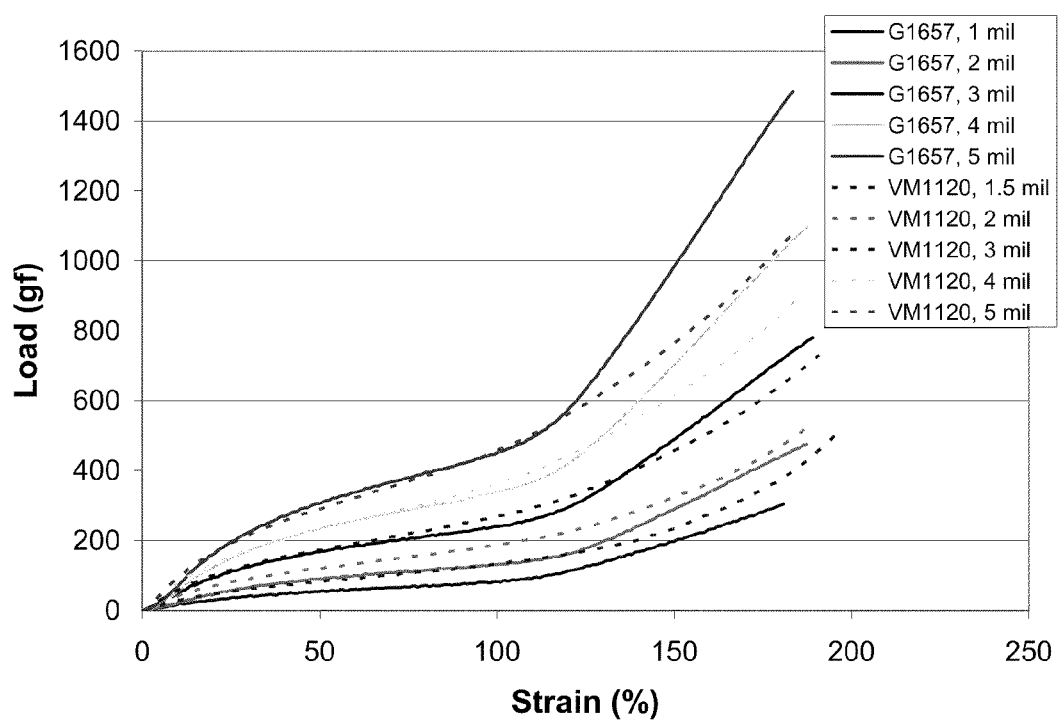
Figure 2. Series of second loading curves for Kraton G1657 and Vistamaxx VM1120 at various gauges.

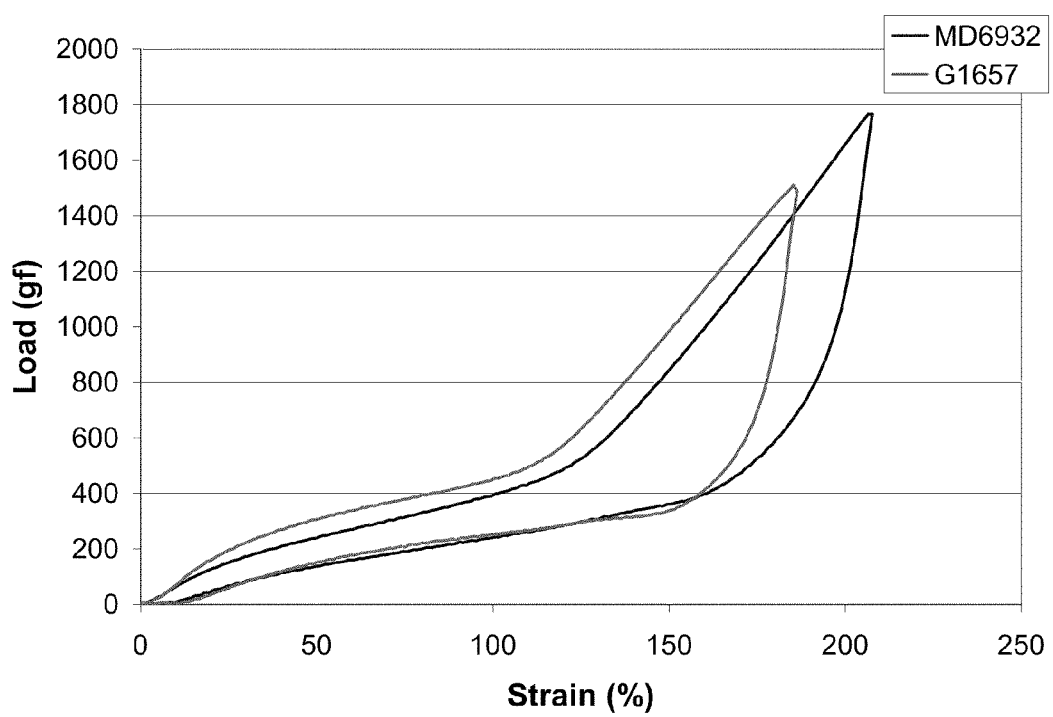
Figure 3. Second cycle hysteresis curve for Kraton MD6932 and G1657.

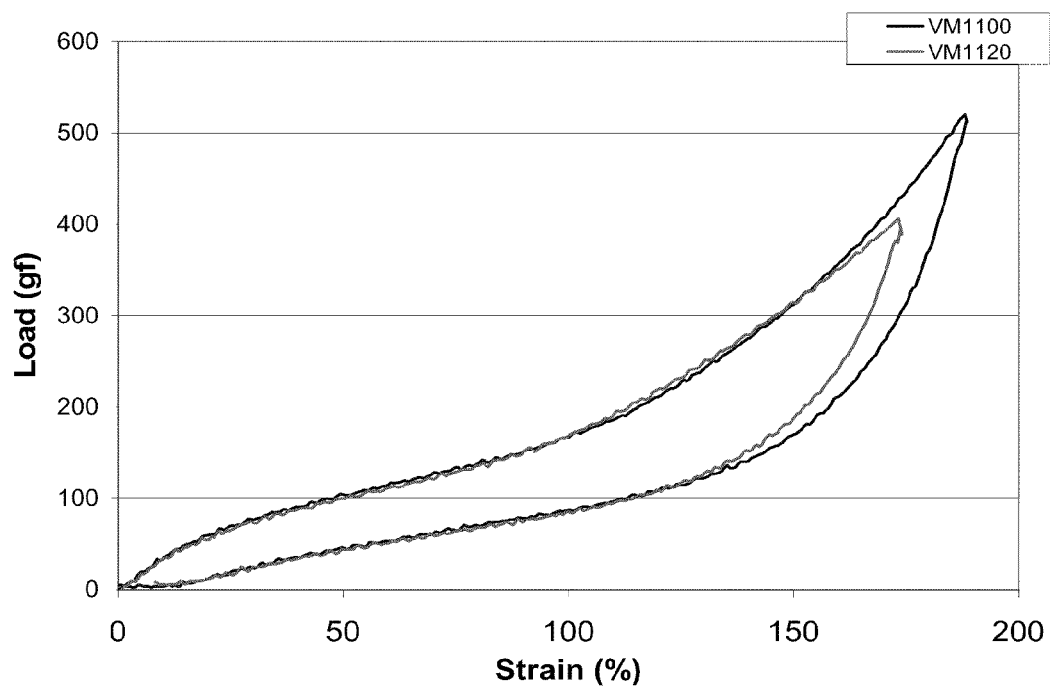
Figure 4. Second cycle hysteresis curve for Vistamaxx VM1100 and VM1120.

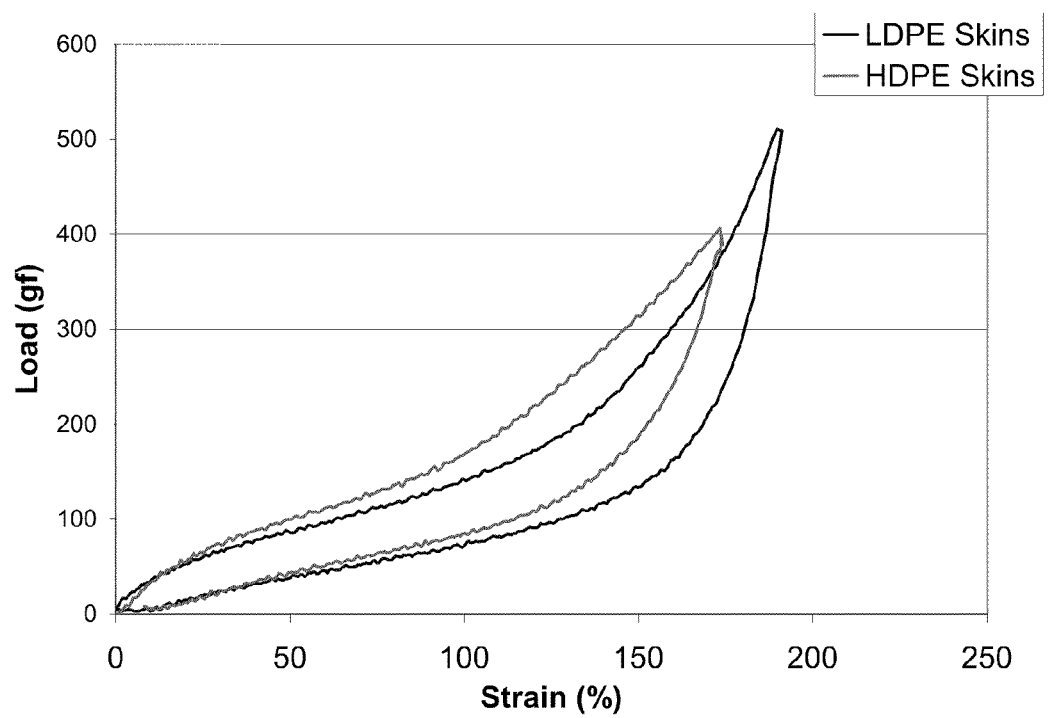
Figure 5. Effect of skin resin type on second cycle hysteresis curve. Elastomer resin is VM1120.

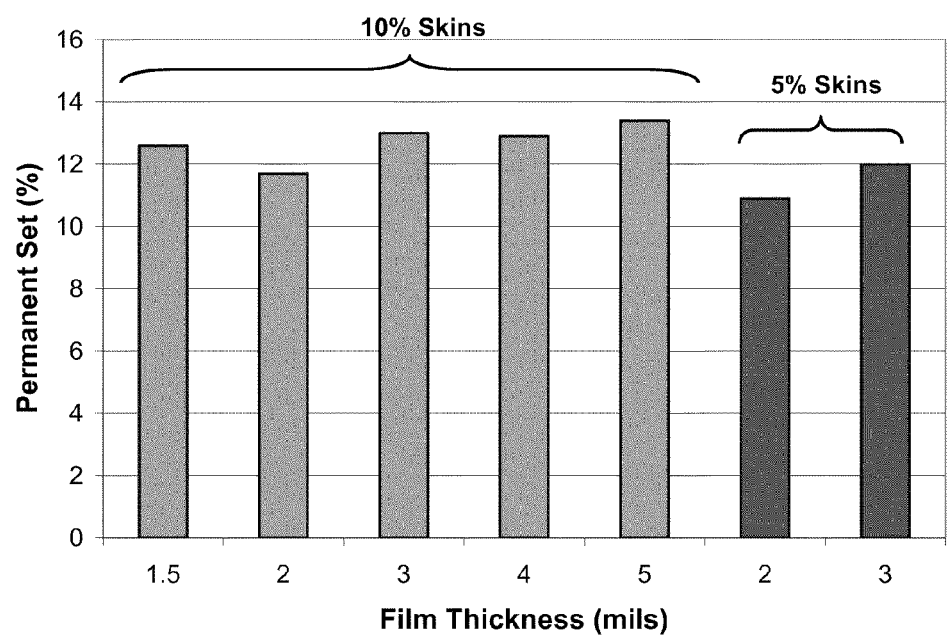
Figure 6. Second cycle permanent set as a function of film thickness and skin layer percent.

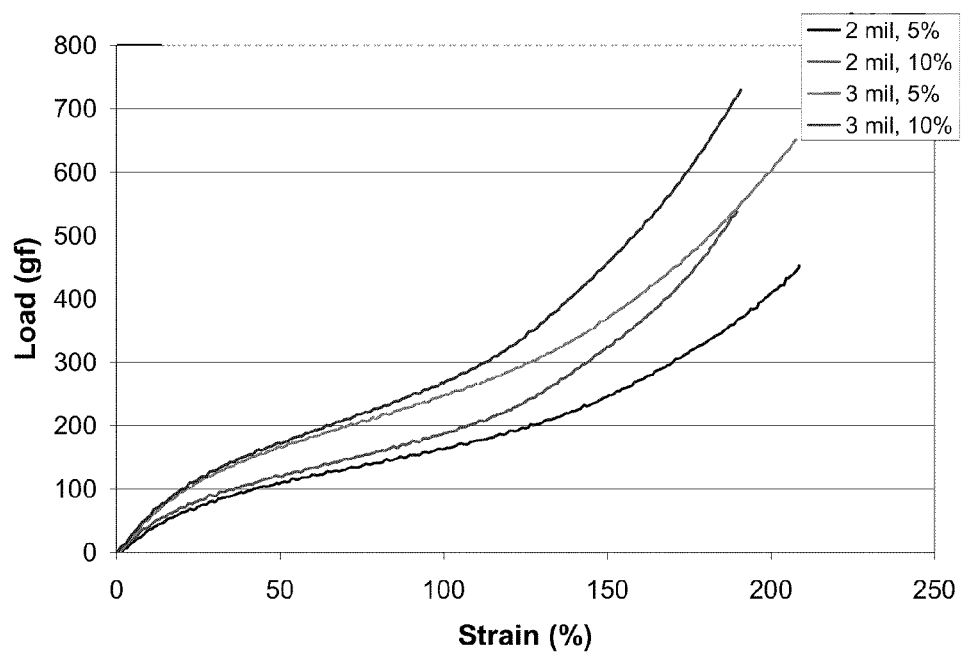
Figure 7. Effect of skin layer percent on second cycle loading curve. Elastomer resin is VM1120.

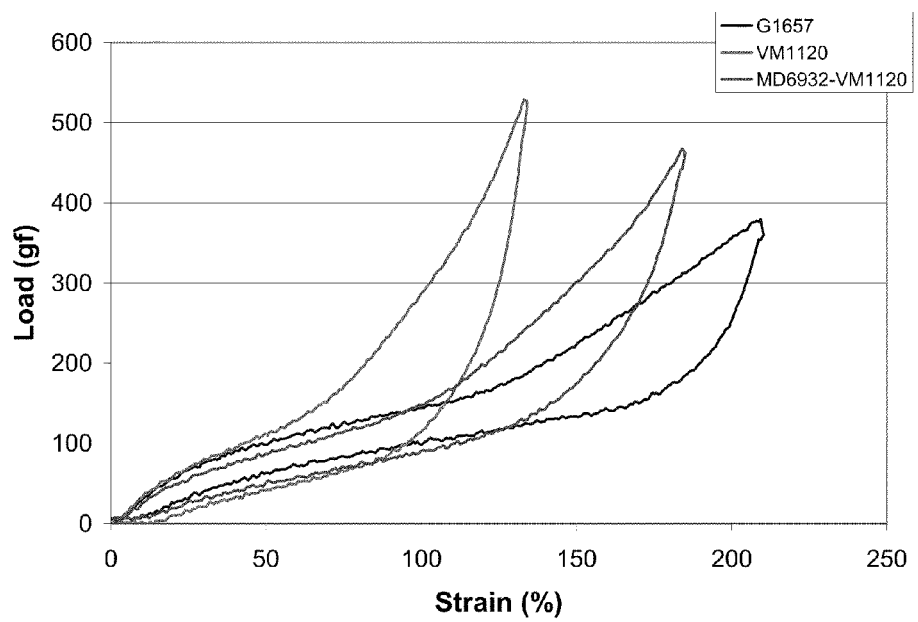
Figure 8. Second cycle hysteresis comparison of film with a coextruded elastic core and films with single elastic resin cores.

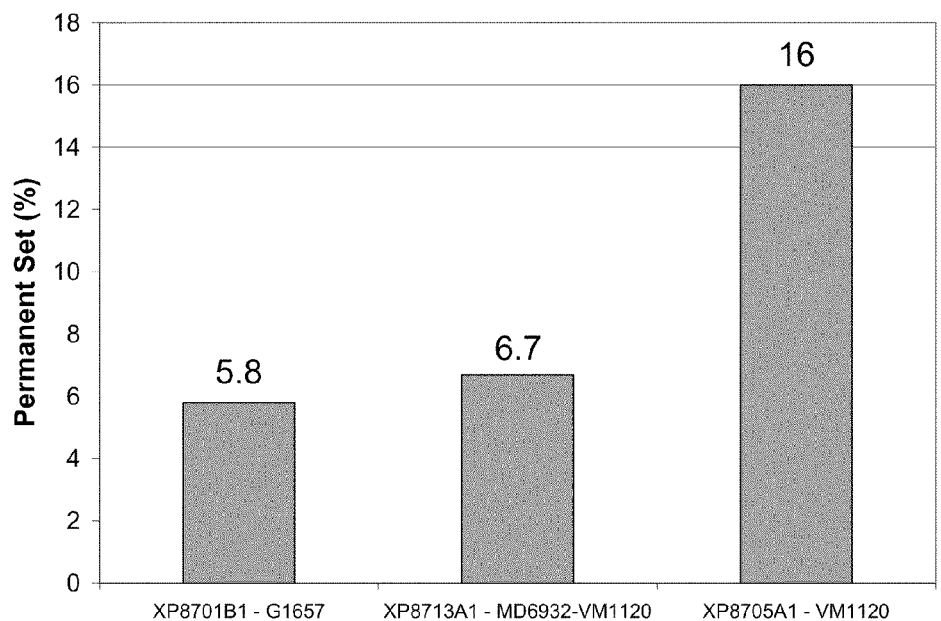
Figure 9. Permanent set comparison of film with a coextruded elastic core and films with single elastic resin cores.

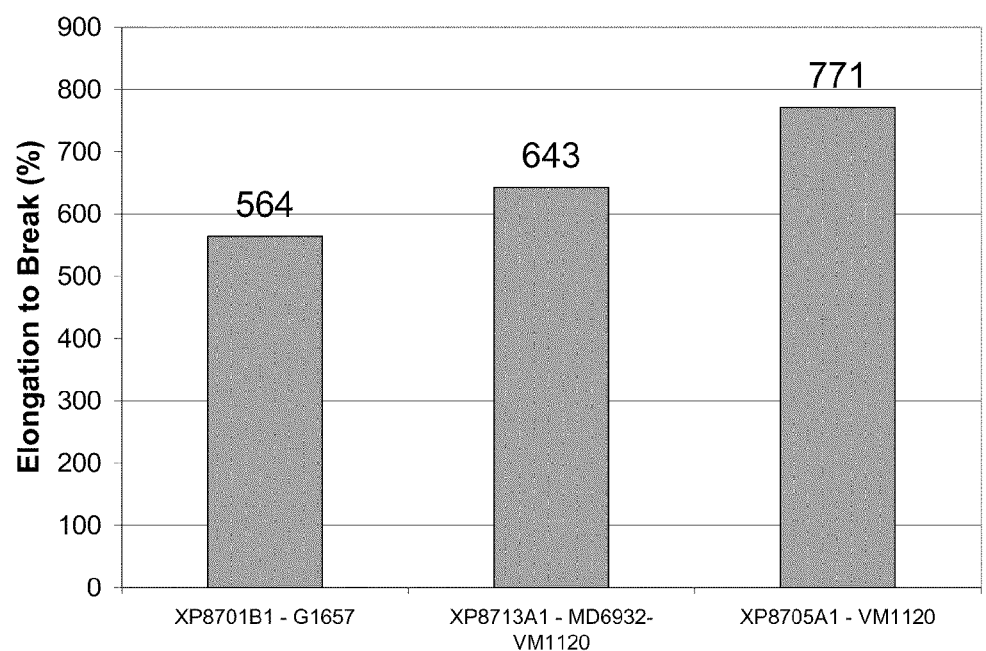
Figure 10. Tensile elongation to break comparison of film with a coextruded elastic core and films with single elastic resin cores.

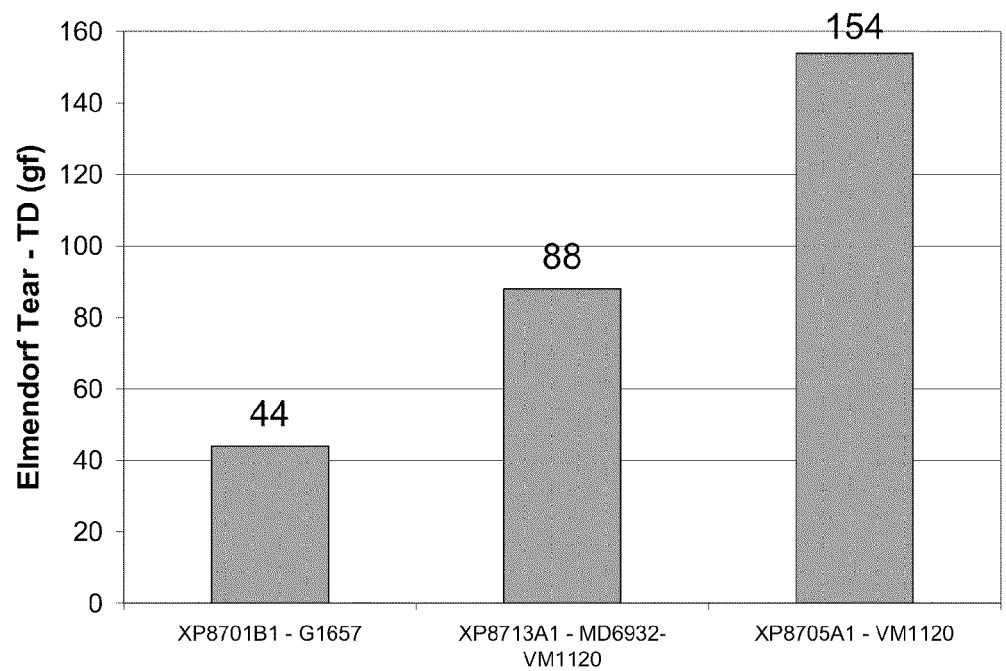
Figure 11. Elmendorf Tear comparison of film with a coextruded elastic core and films with single elastic resin cores.

LOW COST MULTILAYER ELASTOMERIC FILMS HAVING A LOW PERMANENT SET

RELATED APPLICATIONS

This application is a divisional application of U.S. Pat. No. 7,629,278 issued on Dec. 8, 2009, which is related to, and claims benefit of and priority from, Provisional Application Ser. No. 60/692,308 filed on Jun. 20, 2005, titled "Low Cost Multilayer Elastomeric Films Having A Low Permanent Set", the complete subject matter of which is incorporated herein by reference in its entirety.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The presently described technology relates generally to the art of polymer films, and more specifically to multilayer elastomeric films containing styrene block copolymer(s) ("SBC") and a second non-SBC elastomer or plastomer, which exhibit improved film properties in comparison to films comprised of SBC only.

Disposable absorbent articles (e.g., disposable diapers for children or adults) often include elastic features designed to provide enhanced and sustainable comfort and fit to the wearer by conformably fitting to the wearer over time. Examples of such elastic features may include, for example, elastic waist features, elastic leg cuffs, elastic side tabs, or elastic side panels that can provide expansion and contraction benefits to an absorbent article so that the article may conform to the wearer in varying directions. Additionally, such elastic features are often required to be breathable to provide a desired level of comfort to the wearer's skin.

Further, the elastic features of disposable absorbent articles may be made of compound materials comprising elastic films (including breathable films) or elastic scrims, laminated to non-woven fabrics providing desired surface properties and aesthetics of the compound material. The elastic properties of such compound materials are often obtained by activating the elastic properties within the compound, which can be latent before activation, that is the compound material which is non-elastic by itself before the activation becomes elastic after the activation as it were itself elastic.

One of the activation techniques can include mechanical stretching, in particular incremental mechanical stretching. Such mechanical stretching provides permanent elongation of the non-woven substrate(s) comprising the compound material to enable the elastic member(s) of the same compound material (e.g., elastic film or elastic scrim) to stretch under a tension force applied thereto. When the elastic member is allowed to contract, the permanently elongated non-woven fabric wrinkles or shirrs to contract in at least one dimension along with the elastic member. In doing so, the compound material becomes elastic or an elasticized material.

However, the elasticized materials are often expensive because they cannot only include inexpensive elastic materials, but also require difficult processing and handling of elastic members (i.e., elastic films and scrims). Such processing can include additional and expensive cutting and slip steps or procedures. Thus, because the elasticized features are relatively expensive to produce and include, they typically contribute to a higher cost of various articles produced (i.e., absorbent articles containing such elasticized members).

Another method of allegedly enhancing fit and comfort to an absorbent article is to use elastic strands in its construction. Published United States Application No. 2003/0089454 to Johnson, describes methods for the manufacture of absorbent articles utilizing such elastic strips. Although the reference describes the articles as providing a comfortable and contoured fit to the wearer over time, the construction of such articles with elastic strips often results in a bulky side area of the product.

Moreover, elastic strand products and other elasticized materials are often expensive to produce because of the inclusion of expensive elastomeric materials such as a styrene block copolymer, but also require difficult process operations.

There is market interest based upon aesthetic and economic reasons in replacing the Lycra® or styrene block copolymer elastic strands used today with an elastic film. By incorporating an elastic film rather than Lycra® or styrene block copolymer elastic strands it is believed that the absorbent product would exhibit a flatter-looking side panel. Further, using a single roll of elastic film could eliminate the processing problems inherent with handling many spools of elastic strands. Further, elastic films may not be generally a more cost effective alternative to Lycra® elastic materials.

Thus, there is a need for a low cost multilayer elastomeric film having improved tear strength, and elongation to break, while providing a high elastic recovery, as measured by the permanent set, more typical of an SBC elastomeric film.

BRIEF SUMMARY OF THE INVENTION

In light of the problems, difficulties and undesired outcomes described above, a new low cost elastomeric film having a low permanent set for use in elasticized features of various articles, for example disposable absorbent articles, has been discovered. Methods and products resultant from such methods for producing the new low cost elastomeric film having a low permanent set are also described herein.

More specifically, the presently described technology involves elastomeric films, preferably multilayer elastomeric films, containing at least one layer of styrene block copolymer (SBC) and at least one elastomer or plastomer layer substantially free of styrene block copolymer.

Thus in one aspect, the present technology concerns an elastomeric composition containing at least one styrene block copolymer and at least one elastomer or plastomer which is substantially free of styrene block copolymer such that the resultant elastomeric composition has a permanent set substantially equal to or less than an elastomeric composition containing only styrene block copolymer.

In another aspect of the present technology there is provided a polymeric coextruded multilayer film or a multilayer film laminate having at least one layer comprised of a styrene block copolymer and at least one layer consisting essentially of an elastomer or plastomer substantially free of styrene block copolymer. The resultant polymeric coextruded multilayer film or multilayer film laminate has a permanent set substantially equal to or less than a coextruded multilayer film or multilayer film laminate composed of only styrene block copolymer.

A further aspect of the presently described technology also concerns a method of manufacturing a multilayer elastomeric film by coextruding at least one styrene block copolymer layer with at least one elastomer or plastomer layer substantially free of styrene block copolymer, such that the resultant multilayer elastomeric film has a permanent set substantially equal to or less than that of a coextruded multilayer elastomeric film containing one or more layers of styrene block copolymer only.

In yet a further aspect of the present technology there is provided a method of manufacturing a multilayer elastomeric film laminate by laminating at least one styrene block copolymer layer with at least one elastomer or plastomer layer, wherein the resultant multilayer elastomeric film laminate has a permanent set substantially equal to or less than that of a multilayer elastomeric film laminate containing only one or more layers of styrene block copolymer.

A still further aspect of the present technology concerns an absorbent article comprised of a component (for example, a side tab, a side panel, or a waistband) that has at least one non-woven outer layer and at least one elastomeric film inner layer attached to the non-woven outer layer, and the elastomeric film inner layer is comprised of at least one layer of a styrene block copolymer and at least one layer consisting essentially of an elastomer or plastomer. Additionally, the elastomeric film inner layer has a permanent set substantially equal to or less than an elastomeric film inner layer of an absorbent article comprised only of styrene block copolymer.

Moreover, another aspect of the present technology concerns a multilayer elastomeric film having a formulation in each layer. Preferably, in at least one embodiment of the presently described technology there is provided at least one core layer containing between about 1% to about 100%, more preferably about 50% or greater by weight of a styrene block copolymer; at least one inner layer comprised of between about 0% to about 100%, more preferably about 50% or greater, and most preferably about 80% or greater by weight of a ethylene/propylene copolymer, propylene copolymer or combinations thereof that is positioned on at least one side of the core layer; and at least one outer layer comprised of between about 0% to about 100%, more preferably about 50% or greater, and most preferably about 80% or greater by weight of a high or low density polyethylene (or combinations thereof) that is positioned on at least one side of the inner layer. The resultant multilayer elastomeric film has a permanent set substantially equal to or less than the permanent set of a multilayer elastomeric film consisting only of styrene block copolymer.

In yet a further aspect of the present technology, there is provided an elastomeric film having at least one skin layer (which may comprise one or more inner layers and one or more outer layers in relation to a core layer) and at least one core layer which further comprises at least one styrene block copolymer and at least one elastomer or plastomer layer which is substantially free of styrene block copolymer. The layer ratios of the described film are generally from about 20% to about 80%, more preferably 30% to about 75%, most preferably from about 35% to about 65% for the core layer and from about 0% to about 40%, more preferably about 15% to about 35% for each of the inner layers, and from about 0% to about 35%, more preferably less than about 20% for each of the outer layers (which may act as a skin layer). The resultant elastomeric film has a permanent set substantially equal to or less than an elastomeric film containing only styrene block copolymer.

In all of the aspects of the present technology described above, the elastomeric films, laminates, articles and the like have improved properties over conventional elastomeric films comprised of only SBC. The addition of the elastomer or plastomer layer or layers as described herein improves the tear strength and elongation to break of the elastomeric films of the present technology, while providing a high elastic recovery, as measured by the permanent set, more typical of an SBC elastomeric film. Surprisingly, it has been found that the elastomeric films of the presently described technology have a permanent set substantially equal to or less than an elastomeric film containing one or more layers of SBC alone. As a result, the elastomeric films, laminates, and articles of the present technology offer a low cost alternative to more expensive elastomeric films currently available.

BRIEF DESCRIPTION OF SEVERAL VIEWS OF THE DRAWINGS AND/OR FIGURES

While the specification concludes with claims particularly pointing out and distinctly claiming the subject matter, which is regarded as the presently described technology of the present invention, it is believed that the presently described technology will be more fully understood from the following description taken in conjunction with the accompanying figures, in which:

FIG. 1 is a graphical illustration of a first hysteresis curve, "activation curve" for a styrene block copolymer and an ethylene/propylene copolymer.

FIG. 2 is a graphical illustration of a series of second loading curves for styrene block copolymers and ethylene/propylene copolymers at various gauges.

FIG. 3 is a graphical illustration of a second cycle hysteresis curve for styrene block copolymers.

FIG. 4 is a graphical illustration of a second cycle hysteresis curve for ethylene/propylene copolymers.

FIG. 5 is a graphical illustration of the effect of skin resin type on second cycle hysteresis curve for an elastomeric film.

FIG. 6 is a graphical illustration of second cycle permanent set as a function of film thickness and skin layer percent.

FIG. 7 is a graphical illustration of the effect of skin layer percent on second cycle loading curve for an elastomer.

FIG. 8 is a graphical illustration of second cycle hysteresis comparison of films with coextruded elastic cores and films with single elastic resin cores.

FIG. 9 is a graphical illustration of the permanent set comparison of a film with a coextruded elastic core and films with single elastic resin cores.

FIG. 10 is a graphical illustration of a tensile elongation to break comparison of a film with a coextruded elastic core and films with single elastic resin cores.

FIG. 11 is a graphical illustration of an Elmendorf Tear comparison of a film with a coextruded elastic core and films with single elastic resin cores.

DETAILED DESCRIPTION OF THE INVENTION

The elastomeric films, methods of producing such films and articles incorporating the elastomeric films of the presently described technology are suited for a variety of uses and applications, in particular for use in or as garments, such as a disposable absorbent article.

As used herein, the term "absorbent article" refers to a device which absorbs and contains body exudates, and more specifically, refers to a device which is placed against the skin of a wearer to absorb and contain the various exudates discharged from the body. Examples of absorbent articles include diapers, pull-on pants, training pants, incontinence briefs, diaper holders, feminine hygiene garments, and the like.

The term "elastic" or "elastic engine" refers herein to any material that upon application of a force to its relaxed, initial length can stretch or elongate to its elongated length without rupture and breakage, and which can substantially recover its initial length upon release of the applied force.

The phrase "substantially equal" herein refers to any numerical value with a variance of (+) or (−) about 20% from the base numerical value. Thus, one of ordinary skill in the art will recognize that the physical property values (or other values) set forth herein, in particular, permanent set, are capable of being within the spirit and scope of the present technology after consideration of test method error.

The term "elasticized" refers herein to any elastic material comprising one or more elastic components and one or more nonwoven fabrics, which may be activated to provide permanent elongation of the non-woven fabrics to enable the elastic components to stretch under application of a tension force. Additionally, the term "elasticized" can also refer herein to nonwovens that are inherently elastic, but do not require activation. However, such nonwovens are expensive to manufacture. Further the term "elasticized" can also refer herein to nonwovens that are inherently extensible, but do not recover. Such nonwovens can also be made to behave in an elastic manner by laminating them to elastic films. Thus, one of ordinary skill in the art will appreciate that the term "elasticized" can refer to any of the various activated, non-activated, laminated, and inherent elastic compounds and situations noted above.

The term "latent elastic material" refers herein to a compound material which by itself can be substantially non-elastic or partially elastic before activating its latent elastic properties.

The term "compound material" refers herein to any material suitable for use in garments or disposable absorbent articles, which is capable of transmitting air vapor to provide desired comfort to the wearer.

The term "disposable" is used herein to describe absorbent articles, which generally are not intended to be laundered or otherwise restored or reused as absorbent articles, but rather discarded after use by the wearer.

The term "breathable" refers herein to any material for use in garments or disposable absorbent articles, which is capable of transmitting air vapor to provide desired comfort to the wearer.

Thermoplastic materials suitable for use in the elastomeric compositions and films of the present technology are generally materials that flow when heated sufficiently above their glass transition temperature and become solid when cooled.

Thermoplastic materials that have elastomeric properties are typically called elastomeric materials. Thermoplastic elastomeric materials are generally defined as materials that exhibit high resilience and low creep as though they were covalently crosslinked at ambient temperatures, yet process like thermoplastic nonelastomers and flow when heated above their softening point. Thermoplastic elastomeric materials, in particular block copolymers, useful in practicing the presently described technology can include, for example, linear, radial, star, and tapered block copolymers such as styrene block copolymers, which may include, for example, Kraton® or Kraton®-based styrene block copolymers available from Kraton Polymers, Inc., located in Houston, Tex., styrene-isoprene block copolymers, styrene-(ethylene-butylene) block copolymers, styrene-(ethylene-propylene) block copolymers, and styrene-butadiene block copolymers; polyether esters such as that available under the trade designation HYTREL™ G3548 from E.I. DuPont de Nemours; and polyether block amides such PEBAX™ available from Elf Atochem located in Philadelphia, Pa. Preferably, styrene block copolymers are utilized in practicing the presently described technology. Styrene-ethylene butylene block copolymers are most preferred. The styrene block copolymers of the present technology may be used in the described elastomeric film materials in amounts from about 10% to about 50% by weight, based upon the total weight of the film.

Non-styrene block copolymers (elastomers or plastomers) suitable for use in accordance with the presently described technology include, but are not limited to, ethylene copolymers such as ethylene vinyl acetates, ethylene octane, ethylene butene, and ethylene/propylene copolymer or propylene copolymer elastomers, such as those available under the trade designation VISTAMAXX® available from ExxonMobil, located in Irving, Tex., or ethylene/propylene/diene terpolymer elastomers, and metallocene polyolefins such as polyethylene, poly (1-hexane), copolymers of ethylene and 1-hexene, and poly(1-octene); thermoplastic elastomeric polyurethanes such as that available under the trade designation MORTHANE™ PE44-203 polyurethane from Morton International, Inc., located in Chicago, Ill. and the trade designation ESTANE™ 58237 polyurethane from Noveon Corporation, Inc., located in Cleveland, Ohio; polyvinyl ethers; poly-α-olefin-based thermoplastic elastomeric materials such as those represented by the formula —(CH2CHR)x where R is an alkyl group containing about 2 to about 10 carbon atoms; poly-α-olefins based on metallocene catalysis such as ENGAGE™ 8200, ethylene/poly-α-olefin copolymer available from Dow Plastics Co., located in Midland, Mich.; polybutadienes; polybutylenes; polyisobutylenes such as VISTANEX NM L-80, available from Exxon Chemical Co.; and polyether block amides such PEBAX™ available from Elf Atochem located in Philadelphia, Pa. A preferred elastomer or plastomer of the presently described technology is an ethylene/propylene copolymer or polypropylene copolymer. It is also preferable that the non-styrene block copolymer elastomer or plastomer of the presently described technology comprise from about 10% to about 95% by weight of the elastomeric film composition based upon the total weight of the composition. For example, one embodiment of the elastomer or plastomer of the presently described technology may be comprised of a polypropylene copolymer containing from about 50% to about 95% of propylene content.

Additional elastomers which can be utilized in accordance with presently described technology also include, for example, natural rubbers such as CV-60, a controlled viscosity grade of rubber, and SMR-5, a ribbed smoked sheet rubber; butyl rubbers, such as EXXON™ Butyl 268 available from Exxon Chemical Co., located in Houston, Tex.; synthetic polyisoprenes such as CARIFLEX™, available from Shell Oil Co., located in Houston, Tex., and NATSYN™ 2210, available from Goodyear Tire and Rubber Co., located in Akron, Ohio; and styrene-butadiene random copolymer rubbers such as AMERIPOL SYNPOL™ 1101 A, available from American Synpol Co., located in Port Neches, Tex.

Additional thermoplastic materials which may also be useful in practicing the presently described technology that are generally considered nonelastomeric include, for example, polyolefins such as isotactic polypropylene, low density polyethylene, linear low density polyethylene, medium density polyethylene, high density polyethylene, polybutylene, non-elastomeric polyolefin copolymers or terpolymers and blends thereof, ethylene-vinyl acetate copolymers such as those available under the trade designation ELVAX™ from E. I. DuPont de Nemours, Inc., located in Wilmington, Del.; ethylene acrylic acid copolymers; ethylene methacrylic acid copolymers such as those available under the trade designation SURLYN™ 1702 from E.I. DuPont de Nemours, Inc.; polymethylmethacrylate; polystyrene; ethylene vinyl alcohol; polyesters including amorphous polyester; polyamides; fluorinated thermoplastics such as polyvinylidene fluoride; halogenated thermoplastics such as chlorinated polyethylene; polyether-block-amides such as those available under the trade designation PEBAX™ 5533 from Elf-Atochem North America, Inc., located in Philadelphia, Pa. It will be appreciated by those skilled in the art that these additional thermoplastic materials may be utilized in accordance with the spirit and scope of the presently described technology to achieve further desired physical properties of the resultant elastomeric compositions or films.

It will also be appreciated by those skilled in the art that additives may be added to the one or more layers of the presently described film technology in order to improve certain characteristics of the particular layer. Preferred additives include, but are not limited to, color concentrates, neutralizers, process aids, lubricants, stabilizers, hydrocarbon resins, antistatics, and antiblocking agents. It will also be appreciated that a color concentrate may be added to yield a colored layer, an opaque layer, or a translucent layer. A suitable nucleating agent may include, for example, calcium carbonate while a suitable processing aid may include, for example, calcium stearate.

Suitable antistatic agents may include, for example, substantially straight-chain and saturated aliphatic, tertiary amines containing an aliphatic radical having from about 10 to about 20 carbon atoms that are substituted by ω-hydroxy-$(C_1-C_4)$-alkyl groups, and N,N-bis-(2-hydroxyethyl)alkylamines having from about 10 to about 20 carbon atoms in the alkyl group. Other suitable antistatics can include ethoxylated or propoxylated polydiorganosiloxanes such as polydialkylsiloxanes and polyalkylphenylsiloxanes, and alkali metal alkanesulfonates.

Antiblocking agents suitable for use with the presently described film technology include, but are not limited to, calcium carbonate, aluminum silicate, magnesium silicate, calcium phosphate, silicon dioxide, and diatomaceous earth. Such agents can also include polyamides, polycarbonates, and polyesters.

Additional processing aids that may be used in accordance with the presently described technology include, for example, higher aliphatic acid esters, higher aliphatic acid amides, metal soaps, polydimethylsiloxanes, and waxes. Conventional processing aids for polymers of ethylene, propylene, and other α-olefins are preferably employed in the present technology. In particular, alkali metal carbonates, alkaline earth metal carbonates, phenolic stabilizers, alkali metal stearates, and alkaline earth metal stearates are preferentially used as processing aids for the films of the presently described technology.

Additional hydrocarbon resins, and in particular, styrene resins, terpene resins, petroleum resins (including polyethylenes and polypropylenes), nylon resins, ethylene vinyl alcohol resins, and cyclopentadiene resins may also be suitable as additives for use in the described films in order to improve desirable physical properties of the films. These properties may include, for example, water vapor permeability, shrinkage, film rigidity, and optical properties The multilayer films of the presently described technology may be constructed of at least two layers, more preferably at least 3 layers, and even more preferably at least 5 layers. The layers may be continuous or discontinuous. The practical upper limit for the number of layers suitable in the elastomeric film of the presently described technology is up to about 500.

In a preferred embodiment of the presently described film technology described herein, the film structure is a five-layer structure. The five-layer structure allows for a core layer protected by two inner layers, one positioned on either side of the core layer, and two outer layers, one positioned on either non-core facing side of each inner layer. Additionally, the instant five layer structure preferably comprises the following: HDPE/LDPE outer skin layer (90/10) 5% by weight/ VISTAMAXX™ elastomer inner layer 20% by weight/KRATON™ styrene block copolymer core layer 50% by weight/ VISTAMAXX™ elastomer inner layer 20% by weight/ HDPE/LDPE outer skin layer (90/10) 5% by weight, based upon the total weight of the film.

The films of the presently described technology offer a cost competitive, elastomeric composition capable of being used as elastomeric films, coextruded polymeric film, film laminates, and as a component of various articles, such as a disposable absorbent garment (i.e., a nonwoven layer attached to an elastomeric core layer of the present technology). Further, the present technology also offers a low cost elastomeric composition that exhibits improved tear strength and elongation to break, while providing a high elastic recovery, as measured by the permanent set, more typical of an expensive SBC elastomeric film.

Again, it has been surprisingly found that the elastomeric films of the presently described technology have a permanent set substantially equal to or less than an elastomeric film containing one or more layers of SBC alone. As a result, the elastomeric films, laminates, and articles of the present technology offer a low cost alternative to more expensive elastomeric films currently available. Further, the films of the present technology offer good machinability and processability.

In one embodiment, the present technology envisages a laminate having at least one non-woven layer and at least one elastomeric layer laminated to the non-woven layer. Such a laminate can be used, for example, in absorbent products such as disposable undergarments, pants, and the like or as a component for such articles. The elastomeric film layer of the laminate preferably comprises at least one styrene block copolymer and at least one elastomer or plastomer which is substantially free of styrene block copolymer. Further, the resultant elastomeric film layer has a permanent set substantially equal to or less than an elastomeric film layer containing only styrene block copolymer. Moreover, it should be understood by those skilled in the art that the elastomeric film layer may be a single layer or may be a multilayer film laminate of one more layers of styrene block copolymer and one more layers of an elastomer or plastomer substantially free of styrene block copolymer. Additionally, inner and outer skin layering schemes in relation to the core layer for an elastomeric film multilayer laminate are also envisaged. Moreover, it should be understood that the elastomeric films of the presently described technology can have a variety of gauges. Preferably, the gauges of the elastomeric film compositions of the present technology range from about 1 mil to about 5 mils.

To make the elastomeric films of the presently described technology, a variety of known film processing techniques (lamination, coextrusion, and the like) may be utilized. In general, a lamination process requires multiple steps in which discrete layers of polymer are laminated together to arrive at a finished film. However, it should be understood by those skilled in the art that the spirit and scope of the presently described technology envisages the use of a variety of film processing techniques to arrive at the films described herein.

For example, the multilayer films of the presently described technology may also be produced via coextrusion. Using this method, melted and plasticized streams of individual layer materials are fed into a coextrusion die. While in the die, the layers are juxtaposed and combined, after which they emerge from the die in a single multilayer film of polymeric material. Further, coextrusion of the films of the presently described technology may be conducted at temperatures of from about 300° F. to about 550° F.

Additionally, coextrusion techniques may include the use of a feed block with a standard die, a multi-manifold die, such as a circular die, or a multi-manifold die, such as is used in forming flat cast films and cast sheets. The cast film can also be embossed with a texture at the time of extrusion by dropping the molten film web into a nip between a patterned roll (usually steel) and a non-patterned roll (usually silicone or other rubber, and if desired, steel). However, it should be understood by those skilled in the art that the films of the present technology may be embossed or may forego embossing depending upon the type of final film desired. Suitable coextrusion techniques for use in producing the films of the present technology are fully described in U.S. Pat. Nos. 5,139,878 and 4,677,017, which are incorporated by reference in their entirety. The films of the present technology are preferably manufactured utilizing a cast process.

The multilayer films of the present technology may also be made via blown film coextrusion. The film is formed using a blown film apparatus composed of a multi-manifold circular die head having concentric circular orifices. The multilayer film is formed by coextruding a molten layer through a circular die, and a molten layer on the other or each opposite side of the first layer through additional circular dies concentric with the first circular die. Next, a gas, typically air, is blown through a jet that is concentric with the circular dies, thereby forming a bubble that expands the individual layers. The bubble is collapsed onto itself to form a pair of multilayer films attached at two opposite edges. Usually, the pair of attached multilayer films are then cut apart at one or more edges and separated into a pair of multilayer films that can be rolled up.

All documents, e.g., patents and journal articles, cited above and/or below, are hereby incorporated by reference in their entirety. One skilled in the art will recognize that modifications may be made in the presently described technology without deviating from the spirit or scope of the invention. The presently described technology is also illustrated by the following examples which are not to be construed as limiting the invention or scope of the specific procedures or compositions described herein. All levels and ranges, temperatures, results, etc., used and/or described herein are approximations unless otherwise specified.

The invention is further illustrated in the following non-limiting Examples. All proportions in the Examples and elsewhere in the specification are by weight unless specifically stated otherwise. Further, the following examples demonstrate some of the advantages and unique properties of the low cost multi-layer elastic film of the presently described technology.

Examples

Background

Extrusion trials were performed to assess and observe the characteristics of films of the presently described technology and for comparison against conventional films. Kraton styrene block copolymers and ExxonMobil Vistamaxx® ethylene-propylene copolymers were chosen as test materials because both components have among the highest elastic recovery of commercially available elastomers. They are also the most widely used elastic materials in the market today, other than strands. Three layer elastomeric films were developed using each Kraton® (a styrene block copolymer, commercially available from Kraton Polymers, located in Houston, Tex.) and Vistamaxx® (an ethylene/propylene copolymer, propylene copolymer, or combination thereof, commercially available from ExxonMobil, located in Irving, Tex.) based resins. In the film constructions generated, it is believed the Kraton or Vistamaxx layer acted as the "elastic engine" which allows for stretch and recovery properties within the film constructions.

Five layer films were also developed, each film having coextruded elastic cores comprised of Kraton with Vistamaxx on each side. Table I below shows the basic film compositions. In this situation, the "elastic engine" is the composite of Vistamaxx/Kraton/Vistamaxx. Further, all elastomeric films described herein for the extrusion trials were extruded with polyolefin skins. The skins were used to provide strength for down gauging and to prevent the mechanical film rolls from blocking Vistamaxx was extruded with low density polyethylene ("LDPE") and high density polyethylene ("HDPE") skins, and Kraton was extruded with polypropylene ("PP") skins.

Films trials were conducted on cast pilot lines and were run in both embossed and non-embossed configurations. In embossed operation, the embossing roll was a high-release silicone rubber. Further processing conditions are provided in Table I below.

Test Method

Due to the films being tested having polyolefin skins, the films required "activation" before the film can act as an elastomer. For information regarding "activation" of films, see U.S. Pat. No. 5,691,034, which is incorporated by reference herein in its entirety. In general, activation involves stretching the film to a strain of at least 200%. Commercially, the "activation" of a film will occur on commercial film production line, usually during lamination. However, "activation" can be simulated in the laboratory utilizing a multi-cycle tensile hysteresis test. For the extrusion trials discussed herein, the first cycle served as the "activation" cycle.

Tensile hysteresis tests were done using an Instron mechanical tester. Samples strips were cut to a size of 1 inch×4 inches with a gauge length of 2 inches. The films were extended to an extension of 6 inches (300% strain) and then unloaded to 0 inches at a crosshead speed of 10 inches/minute. This was done for two complete cycles.

Results

Physical Properties Observed

First cycle hysteresis curves are shown in FIG. 1 below for Kraton and Vistamaxx. The permanent set on the first cycle controls the maximum elongation of the film in use on an absorbent product. In FIG. 1, Kraton had a lower permanent set after the first cycle, which means an absorbent product made with Kraton will have a larger maximum elongation compared to Vistamaxx for a given strain.

FIG. 2 below shows a second cycle loading curve of Vistamaxx and Kraton films at similar gauges, in a range from about 1 to about 5 mils. Both elastic resins provided similar force at equivalent gauge. Further, the skin resin appeared to have minimal or no effect on the force curves. The skin resins for the film samples were PP for Kraton and LDPE for Vistamaxx. FIG. 2 shows that the "elastic engine" controls the loading forces for the three layer films tested.

FIG. 3 below shows Kraton MD6932 and G1657 second cycle hysteresis curves overlaid at a gauge of 5 mils. Additionally, FIG. 4 below shows Vistamaxx 1100 and 1120 second cycle hysteresis curves overlaid at a gauge of 1.5 mils. In both cases, there is minimal or no difference between the elastomers, which are from the same chemical family. It should be noted and appreciated by those skilled in the art, however, that there is a large difference in the set between FIGS. 3 and 4, as would be expected between these two chemical families.

FIG. 5 below shows the effect of skin resin type on Vistamaxx VM1120. The second cycle hysteresis curve is given for VM1120 with LDPE and HDPE skins. The film with HDPE provided a slightly higher force compared with LDPE, but the permanent set was unaffected. Such a result as provided in FIG. 5 indicates that the Vistamaxx layer is controlling the permanent set outcome of the produced films. Further, second cycle permanent set data is provided for in FIG. 6 below for VM1120 films. As can be seen in FIG. 6, the set is relatively unaffected by film thickness. However, decreasing the skin percentage from 10% to 5% reduced the permanent set slightly.

The effect of skin layer ratio was also examined for the Vistamaxx films. The loading force after activation is shown for VM1120 at 2 and 3 mil gauge with total skin percentages of 5 and 10% is shown in FIG. 7 below. At lower strains (<100%), the skin percentage had a minimal effect, again showing the ability of the Vistamaxx layer to act as an "elastic engine" control for elastomeric film or material. At higher strains, the higher skin percentage requires higher force to continue elongation.

An overlay of Kraton G1657 and Vistamaxx VM1120 is shown in FIG. 8 below. It should be noted and appreciated by those skilled in the art that Kraton has much lower force at higher strain as compared to Vistamaxx. Additionally, the permanent set for Kraton is about half of the permanent set for that of Vistamaxx. Such an outcome as illustrated in FIG. 8 demonstrates that the "elastic engine" controls the stretch and recovery properties of the three layer film produced. A five layer structure containing a coextruded elastic core is also shown in FIG. 8. The core is a three layer coextrusion having Kraton MD6932 in the center with Vistamaxx VM1100 on either side. This film has HDPE skins (see Table I below).

The permanent set for the three films of FIG. 8 is provided in FIG. 9 below. Surprisingly, the five layer film has a permanent set similar to that of pure Kraton film rather than that of a pure Vistamaxx film, despite both elastomers being present in the structure. It will be appreciated by those skilled in the art that multiple resin films such as a coextrusion of Vistamaxx and Kraton, in general, will generate resultant physical properties which are an average of the two separate elastomers' physical properties. Surprisingly, this result did not occur with respect to permanent set utilizing the films of the present technology as illustrated in FIGS. 8 and 9. As observed, the five layer film had the advantage of providing a low force to extend and low permanent set, while providing a higher elongation to break and TD tear strength than a film of Kraton alone could provide.

The elongation to break and Elmendorf tear strength data are given below in FIGS. 10 and 11, respectively. The graphs of FIGS. 10 and 11 illustrate that the properties of the five layer structure are an average of the properties of the two elastomers. As noted above, this outcome is typically expected in coextruded structures.

Discussion

Extrusion trials with three layer Kraton-containing films demonstrated that an A/B/A structure with 8 percent total skins (5/90/5) allowed the films to be extruded and down gauged with standard processing conditions.

With 10% total HDPE skins, Vistamaxx resins were able to be down gauged to 1.25 mils. The higher melt strength of Vistamaxx also allowed for reducing the skins to 5% (2.5/95/2.5). Further, the five layer structures using both Vistamaxx and Kraton had the following structure: HDPE/LDPE (90/10) 5%/Vistamaxx 20%/Kraton 50%/Vistamaxx 20%/HDPE/LDPE (90/10) 5%. It was observed that such five layer films were able to be down gauged to 1.25 mils during standard processing. In this respect, the Vistamaxx melt strength enhanced the properties of the five layer structure. This result is surprising given the presence of a Kraton central layer. Although not wanting to be bound by any particular theory, it is believed the inclusion or incorporation of an elastomer or plastomer such as ethylene/propylene copolymer, propylene copolymer, or combination thereof, with a styrene block copolymer can result in an elastomeric film having a permanent set substantially equal to or less than an elastomeric film containing styrene block copolymer only. In addition, the five layer structure as discussed above (see FIGS. 8-11 below) with two elastomers has the further advantage, as mentioned previously, of processability and down gauging to lower film thickness.

TABLE I

Film Structures

| Layers | Elastic Core | Elastic Resin Grades | Skin Resin |
|---|---|---|---|
| 3 | ExxonMobil "Vistamaxx ®" | VM1100 VM1120 | HDPE LDPE, HDPE |
| 3 | Kraton Polymers "Kraton ®" | MD6932 G1657 | PP PP |
| 5 | VM/Kraton/VM | VM1120/MD6932/VM1120 VM1100/G1657/VM1100 | HDPE HDPE |

TABLE II

Processing Temperatures for Elastic Films (° F.)

|  | Kraton | Vistamaxx |
|---|---|---|
| Barrel Zone 1 | 370 | 300 |
| Barrel Zone 2 | 390 | 330 |
| Barrel Zone 3 | 420 | 350 |
| Barrel Zone 4 | 420 | 370 |
| Barrel Zone 5 | 420 | 400 |
| Die Zone (1-5) | 420 | 400 |
| Melt Temp 1 | 435 | 400 |
| Melt Temp 2 | 415 | 400 |
| Chill Roll Temp | 50-55 | 50-55 |

* Temps in ° F.

TABLE III

Description of films of the presently described technology.

| | | Permanent Set | |
|---|---|---|---|
| Elastic Core Resin | Gauge (mil) | Cycle 1 | Cycle 2 |
| G1657 | 1.5 | 30.0% | 5.8% |
| VM1120 | 1.5 | 75.0% | 16.0% |
| VM1100 | 1.5 | 50.0% | 13.6% |
| VM1100 | 1.25 | 53.0% | 13.3% |

TABLE III-continued

Description of films of the presently described technology.

| Elastic Core Resin | Gauge (mil) | Permanent Set | |
| --- | --- | --- | --- |
| | | Cycle 1 | Cycle 2 |
| VM1100/G1657/VM1100 | 1.5 | 40.0% | 8.1% |
| VM1120/MD6932/VM1120 | 1.5 | 41.0% | 6.7% |
| VM1120/MD6932/VM1120 | 1.25 | 42.0% | 7.8% |

The presently described technology and the manner and process of making and using it, are now described in such full, clear, concise and exact terms as to enable one of ordinary skill in the art to which the present technology pertains, to make and use the same. It should be understood that the foregoing describes some embodiments and advantages of the invention and that modifications may be made therein without departing from the spirit and scope of the presently described technology as set forth in the claims. Moreover, the invention has been described with reference to preferred and alternate embodiments. Modifications and alterations will occur to others upon the reading and understanding of the specification. It is intended to include all such modifications and alterations insofar as they come within the scope of the appended claims or equivalents thereof. To particularly point out and distinctly claims the subject matter regarded as the invention, the following claims conclude this specification.

What is presently claimed is:

1. A method of manufacturing a laminate, the method comprising the step of:
   laminating at least one non-woven layer and at least one multilayer elastomeric film layer wherein the multilayer elastomeric film comprises:
      (a) a core layer comprising:
         at least one styrene block copolymer layer; and
         at least one elastomer or plastomer layer which is substantially free of styrene block copolymer, and
      (b) at least one polyolefin polymer skin layer positioned on at least one side of the core layer,
   wherein the multilayer elastomeric film has a permanent set substantially equal to an elastomeric film having a core layer containing only styrene block copolymer.

2. The method of claim 1, wherein the method further comprises the step of providing an additive for inclusion with or incorporation into the laminate.

3. The method of claim 2, wherein the additive is selected from the group consisting of: color concentrates, neutralizers, process aids, lubricants, stabilizers, hydrocarbon resins, antistatics, viscosity reducing polymers, plasticizers, antioxidants, bonding aids, slip agents, heat stabilizers, photostabilizers, glass bubbles, microfibers, and antiblocking agents.

4. A method of manufacturing an elastomeric film, the method comprising the step of:
   coextruding at least one skin layer and at least one core layer;
   wherein the core layer comprises at least one styrene block copolymer layer; and
   at least one elastomer or plastomer layer which is substantially free of styrene block co-polymer, the elastomer or polymer having a higher permanent set than that of the styrene block copolymer, and
   wherein the elastomeric film has a permanent set substantially equal to an elastomeric film having a core layer containing only styrene block copolymer.

5. The method of claim 4, wherein the at least one styrene block copolymer layer comprises from about 35% to about 65% by weight of the film, the at least one elastomer or plastomer layer comprises from about 15% to about 35% by weight of the film, and the at least one skin layer comprises less than about 20% by weight of the film.

6. The method of claim 4, wherein the skin layer is a polyolefin skin.

7. The method of claim 6, wherein the polyolefin skin comprises high density polyethylene, low density polyethylene or mixtures thereof.

8. The method of claim 4, wherein the method further comprises the step of providing an additive for inclusion with or incorporation into the film,
   wherein the additive is selected from the group consisting of: color concentrates, neutralizers, process aids, lubricants, stabilizers, hydrocarbon resins, antistatics, viscosity reducing polymers, plasticizers, antioxidants, bonding aids, slip agents, heat stabilizers, photostabilizers, glass bubbles, microfibers, and antiblocking agents.

9. The method of claim 4, wherein the method further includes the step of casting the multilayer elastomeric film.

10. The method of claim 4, wherein the method further includes the step of cast embossing the multilayer elastomeric film.

11. A method of manufacturing a multilayer elastomeric film, the method comprising the steps of:
   (a) coextruding a core layer comprising an inner core layer containing a styrene block copolymer, and two outer core layers containing a non-styrene block copolymer elastomer or plastomer, wherein one outer core layer is positioned on one side of the inner core layer and the other outer core layer is positioned on the other side of the inner core layer such that the inner core layer is sandwiched between each outer core layer, each outer core layer being substantially free of styrene block copolymer, and
   (b) coextruding two skin layers positioned one on each side of the core layer, the skin layers comprising at least one polyolefin polymer,
   wherein the non-styrene block copolymer elastomer or plastomer comprising the outer core layer has a higher permanent set than the styrene block copolymer comprising the inner core layer, and wherein the multilayer elastomeric film has a permanent set substantially equal to that of a multilayer film having a core layer comprised only of styrene block copolymer.

12. The method of claim 11, wherein the non-styrene block copolymer elastomer or plastomer is a thermoplastic polyolefin, thermoplastic polyurethane, or polyvinyl ether.

13. The method of claim 12, wherein the thermoplastic polyolefin is an ethylene/propylene copolymer or a polypropylene copolymer.

14. The method of claim 11, wherein the polyolefin skin layers comprise high density polyethylene, low density polyethylene or combinations thereof.

15. The method of claim 11, wherein the method further comprises the step of providing an additive for inclusion with or incorporation into the film.

16. The method of claim 15, wherein the additive is selected from the group consisting of: color concentrates, neutralizers, process aids, lubricants, stabilizers, hydrocarbon resins, antistatics, viscosity reducing polymers, plasticizers, antioxidants, bonding aids, slip agents, heat stabilizers, photostabilizers, glass bubbles, microfibers, and antiblocking agents.

17. The method of claim 11, wherein the inner core layer comprises from about 35% to about 65% by weight of the film, each outer core layer comprises from about 15% to about 35% by weight of the film, and each skin layer comprises less than about 20% by weight of the film.

18. The method of claim 11, wherein the method further includes the step of casting the multilayer elastomeric film.

19. The method of claim 11, wherein the method further includes the step of cast embossing the multilayer elastomeric film.

20. A component for an absorbent article comprising:
at least one non-woven outer layer; and
at least one elastomeric film inner layer attached to the non-woven outer layer wherein the elastomeric film inner layer comprises:
  (a) a core layer comprising:
    at least one styrene block copolymer layer; and
    at least one elastomer or plastomer layer which is substantially free of styrene block copolymer, and
  (b) at least one polyolefin polymer skin layer positioned on at least one side of the core layer,
wherein the multilayer elastomeric film has a permanent set substantially equal to an elastomeric film having a core layer containing only styrene block copolymer.

* * * * *